United States Patent
Lee

(10) Patent No.: US 9,017,344 B2
(45) Date of Patent: Apr. 28, 2015

(54) SYRINGE FOR INJECTING SURGICAL THREAD

(76) Inventor: Hee Young Lee, Jeollabuk-do (KR)

( * ) Notice: Subject to any disclaimer, the term of this patent is extended or adjusted under 35 U.S.C. 154(b) by 792 days.

(21) Appl. No.: 13/263,240

(22) PCT Filed: Apr. 23, 2010

(86) PCT No.: PCT/KR2010/002550
§ 371 (c)(1),
(2), (4) Date: Oct. 6, 2011

(87) PCT Pub. No.: WO2010/123305
PCT Pub. Date: Oct. 28, 2010

(65) Prior Publication Data
US 2012/0035624 A1  Feb. 9, 2012

(30) Foreign Application Priority Data

Apr. 24, 2009 (KR) .................. 10-2009-0036088

(51) Int. Cl.
| | |
|---|---|
| *A61B 17/10* | (2006.01) |
| *A61B 17/04* | (2006.01) |
| *A61M 37/00* | (2006.01) |
| *A61B 17/062* | (2006.01) |
| *A61B 17/00* | (2006.01) |
| *A61B 17/06* | (2006.01) |

(52) U.S. Cl.
CPC .......... *A61B 17/0483* (2013.01); *A61B 17/062* (2013.01); *A61B 2017/00761* (2013.01); *A61B 2017/00792* (2013.01); *A61B 2017/00969* (2013.01); *A61B 2017/06052* (2013.01); *A61B 2017/06176* (2013.01); *A61M 37/0069* (2013.01)

(58) Field of Classification Search
USPC ............ 606/139, 185, 187, 107; 604/60, 187, 604/218
See application file for complete search history.

(56) References Cited

U.S. PATENT DOCUMENTS

| | | | |
|---|---|---|---|
| 6,200,296 B1 | 3/2001 | Dibiasi et al. | |
| 2003/0004491 A1* | 1/2003 | Tenhuisen et al. | ............ 604/502 |
| 2006/0184135 A1 | 8/2006 | Prais et al. | |
| 2006/0211982 A1* | 9/2006 | Prestrelski et al. | ............ 604/60 |

FOREIGN PATENT DOCUMENTS

| | | |
|---|---|---|
| KR | 20-0383707 Y1 | 5/2005 |
| KR | 10-0551740 B1 | 2/2006 |

* cited by examiner

*Primary Examiner* — Thomas McEvoy
(74) *Attorney, Agent, or Firm* — Sughrue Mion, PLLC

(57) ABSTRACT

Disclosed is a syringe for injecting a surgical thread. The syringe includes a needle part, a connection part and an injection part. The needle part is adapted to penetrate the skin while accommodating a surgical thread. The connection part is connected to the needle part by taper coupling and is fixedly fastened to the needle part by turning operation of the needle part. The injection part is coupled to the connection part at the front end thereof. A push needle installed in the injection part pushes the surgical thread accommodated in the needle part to inject the surgical thread into a skin tissue in a syringe operation manner.

5 Claims, 8 Drawing Sheets

(a)

(b)

SYRINGE FOR INJECTING SURGICAL THREAD

CROSS REFERENCE TO RELATED APPLICATIONS

This application is a National Stage of International Application No. PCT/KR2010/002550, filed on Apr. 23, 2010, which claims priority from Korean Patent Application No. 10-2009-0036088, filed on Apr. 24, 2009, the contents of all of which are incorporated herein by reference in their entirety.

TECHNICAL FIELD

The present invention relates to a syringe for injecting a surgical thread. More specifically, the present invention relates to a syringe for injecting a surgical thread which includes a needle part adapted to accommodate a surgical thread and an injection part adapted to inject the surgical thread into the skin, the two parts being coupled to each other in a quick and precise manner.

BACKGROUND ART

Numerous syringes for transplanting plastic surgical threads to the human skin in plastic surgical treatments have been proposed according to their applications.

Transplantation syringes for use in plastic surgical treatment are broadly classified into two types: syringes for injecting plastic surgical threads into the skin to remove wrinkles such as facial wrinkles; and syringes for transplanting hairs to the scalp.

The first type of syringes are medical instruments designed to insert surgical threads into the epidermal layer of the skin.

Collagen fibers of the skin are currently used as surgical threads for wrinkle removal. Collagen fibers are micrometer-sized units and are arranged in various directions. Collagen fibers have a certain modulus of elasticity and some extensibility due to the presence of elastin as an elastic component positioned therebetween.

A typical syringe for injecting a surgical thread into the human skin includes a hollow cylindrical injection part and a surgical thread accommodated in the injection part and having a plurality of directional projections.

The syringe includes an insertion part through which a pressure is applied to insert the surgical thread into the human body.

The syringe is operated as follows. First, the surgical thread is loaded in the injection part. Then, the insertion part is coupled to the injection part. When the injection part penetrates a human skin tissue, the insertion part is pressurized to push the surgical thread loaded in the injection part. As a result, the surgical thread is inserted into the soft tissue of the skin.

After the surgical thread loaded in the syringe is injected into the skin, there is a need to load another surgical thread in the syringe for continuous surgical treatment. This troublesome operation makes rapid surgery difficult.

Further, since the surgery time is excessively extended, a subject to be treated should be in an anaesthetic state for a prolonged period of time.

Korean Patent No. 10-417829 proposes a syringe for hair transplantation. The hair transplanter includes: a needle having a through-hole to accommodate a hair root and a groove, through which the hair passes from the through-hole, formed at the front end thereof; a press support connected to the needle and extending backward; a grip part accommodating and fixed to the needle and the press support; a sliding member having a front portion accommodating the needle and a press portion fixing one end of the press support and being accommodated in the grip part at the center thereof so as to be movable when a force is applied to the press portion; a guide plate provided at the front end of the sliding member so as to correspond to and be inserted into the groove of the needle, and a spring member provided in the grip part and the sliding member to restore the sliding member.

The hair transplanter is operated in such a manner that when the needle is inserted into and withdrawn from the scalp, the top end of the hair root is latched by the guide plate and the hair root transplanted to the scalp is prevented from being pulled out together with the needle.

However, the prior art hair transplanter also suffers from the same problem as the syringe for injecting a surgical thread for wrinkle removal in that after hair roots are loaded separately in the hair transplanter, the transplantation of the hair roots is repeatedly performed, making it impossible to quickly transplant the hair roots.

DISCLOSURE

Technical Problem

It is, therefore, an object of the present invention to provide a syringe constructed such that needles penetrating the skin can be quickly exchanged in a state in which surgical threads are accommodated.

It is another object of the present invention to provide a syringe constructed such that a needle can be hermetically coupled by turning operation after quick temporal coupling.

It is still another object of the present invention to provide a syringe constructed such that a surgical thread can be injected into a skin tissue without error.

Technical Solution

According to an aspect of the present invention, there is provided a syringe for injecting a surgical thread, including: a needle part adapted to penetrate the skin while accommodating a surgical thread; a connection part connected to the needle part by taper coupling and fixedly fastened to the needle part by turning operation of the needle part; and an injection part coupled to the connection part at the front end thereof to allow a push needle installed therein to push the surgical thread accommodated in the needle part and to inject the surgical thread into a skin tissue in a syringe operation manner.

The needle part includes a needle having an injection hole to accommodate a surgical thread therein and coupling means having a tapered coupling space formed therein to allow the needle to be coupled to one side thereof and a stepped latching portion protruding from the wide tapered end of the coupling space.

The injection part includes a housing having a hole formed therein, a rod coupled to and linearly reciprocating along the hole, and a push needle coupled to the front end of the rod and cooperating with the rod to enter the injection hole.

A spring is accommodated along the inner circumference of the hole of the housing, is latched by a stopper fixed to the outer circumference of the rod, and is compressed by the coupling between the injection part and the connection part so that the push and push-back operation of the rod in the injection part is elastically maintained.

The connection part includes: an introduction portion having an inclined outer circumference adapted to be introduced into the coupling space of the coupling means to allow for primary taper coupling to the needle part and a connection hole formed at the center thereof to be in communication with the injection hole of the needle; a flange spaced outwardly from the introduction portion to create a fixing space therebetween and having a female-threaded portion formed on the inner circumference of the fixing space so as to be fixedly fastened to the needle part by turning operation after the stepped latching portion is engaged with the female-threaded portion; and a fastening portion having a fastening space formed at the rear of the flange and fixedly fastened to the front end of the injection part in the fastening space.

Advantageous Effects

As is apparent from the above description, the needle part adapted to accommodate a surgical thread is easily coupled to or decoupled from the injection part adapted to inject the surgical thread into a skin tissue by sequential taper coupling and turning ("push down & turn"), simultaneously ensuring ease of coupling and hermetic fixing of the needle part. In contrast, frequent exchange of needle parts is inevitable in conventional syringes for injecting surgical threads. Therefore, the needle part can be quickly replaced with an extra needle part accommodating a new surgical thread, thus effectively shortening the time needed to inject the surgical thread.

In addition, double coupling between the needle part and the injection part helps to precisely introduce the push needle into the injection hole. Therefore, when the needle loaded with a thread is detached, the need for manual coupling of the push needle to the needle is eliminated. That is, the coupling of the push needle to the needle is automated, unlike a conventional hair transplanter where a push needle is coupled to an injection hole and is subsequently coupled to another element, Due to this construction, the time required to detach the needle is greatly reduced.

Furthermore, the syringe of the present invention is constructed to visually check the moving distance of the rod. Due to this construction, the injection depth of a surgical thread can be measured, enabling more accurate and effective surgical treatment.

<Explanation of main reference numerals>

Figure 1:
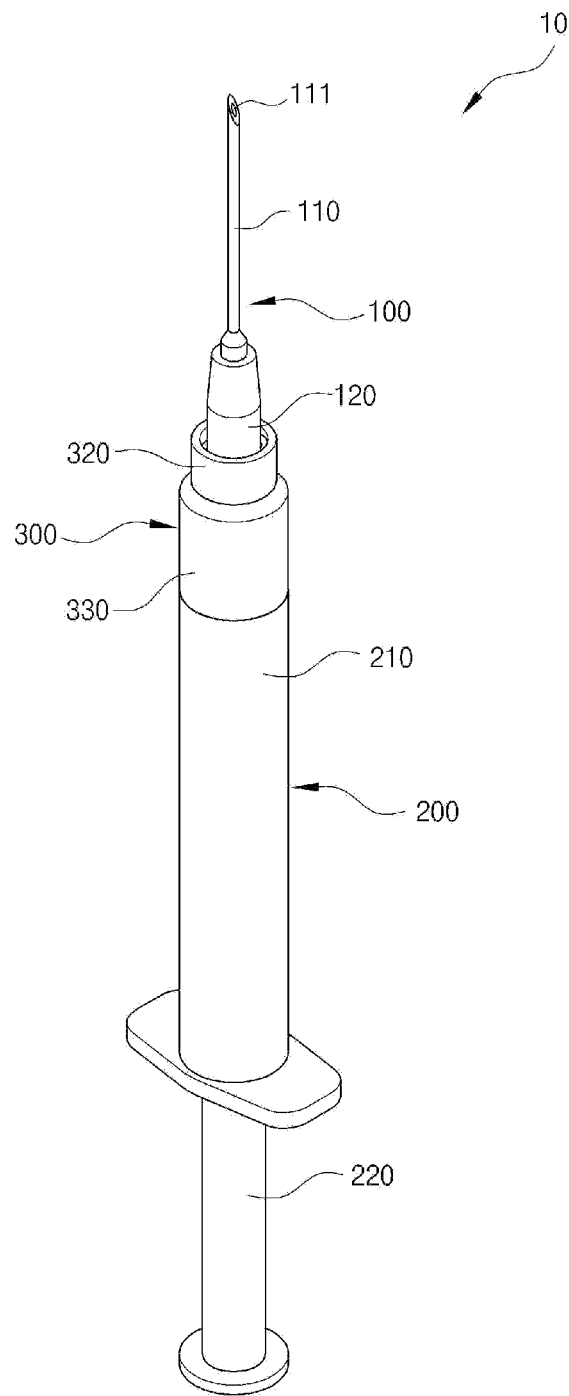
FIG. 1 is a perspective view illustrating a syringe for injecting a surgical thread according to an embodiment of the present invention.

| | | | |
|---|---|---|---|
| 10: | Syringe | 11: | Surgical thread |
| 100: | Needle part | 110: | Needle |
| 111: | Injection hole | 120: | Coupling means |
| 121: | Stepped latching portion | 122: | Coupling space |
| 123: | Through-hole | 200: | Injection part |
| 210: | Housing | 211: | Hole |
| 220: | Rod | 221: | Push needle |
| 222: | Stopper | 223: | Closing stop |
| 224: | Sealing ring | 225: | Stop portion |
| 300: | Connection part | 310: | Introduction portion |
| 311: | Connection hole | 320: | Flange |
| 321: | Fixing space | 322: | Female-threaded portion |
| 330: | Fastening portion | 331: | Fastening space |
| 340: | Spring | | |

MODE FOR INVENTION

Preferred embodiments of the present invention will now be described in detail with reference to the accompanying drawings. It should be noted that whenever possible, the same reference numerals will be used throughout the drawings and the description to refer to the same or like parts. In describing the present invention, detailed descriptions of related known functions or configurations are omitted in order to avoid making the essential subject of the invention unclear.

Figure 2:
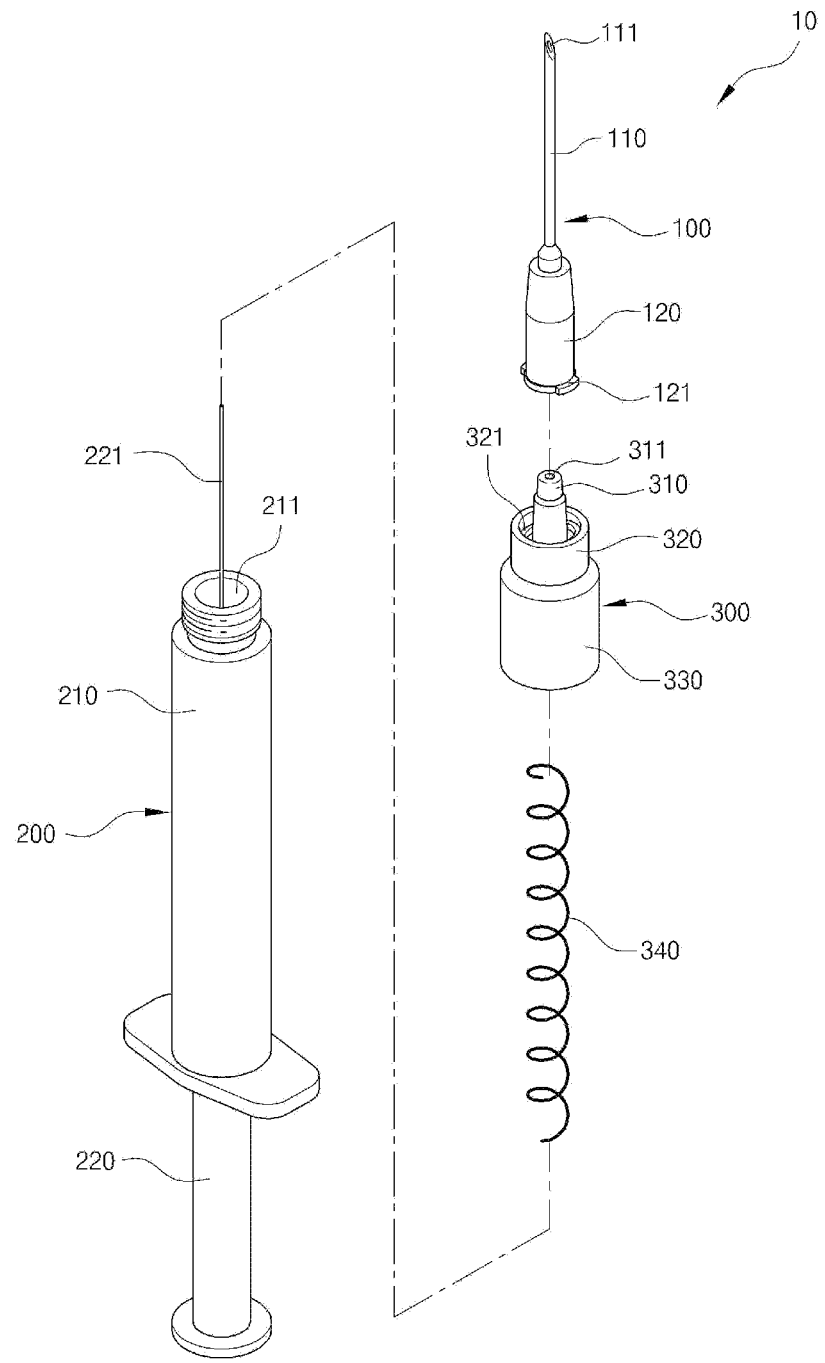
FIG. 2 is an exploded perspective view illustrating the syringe of FIG. 1.
Figure 3:
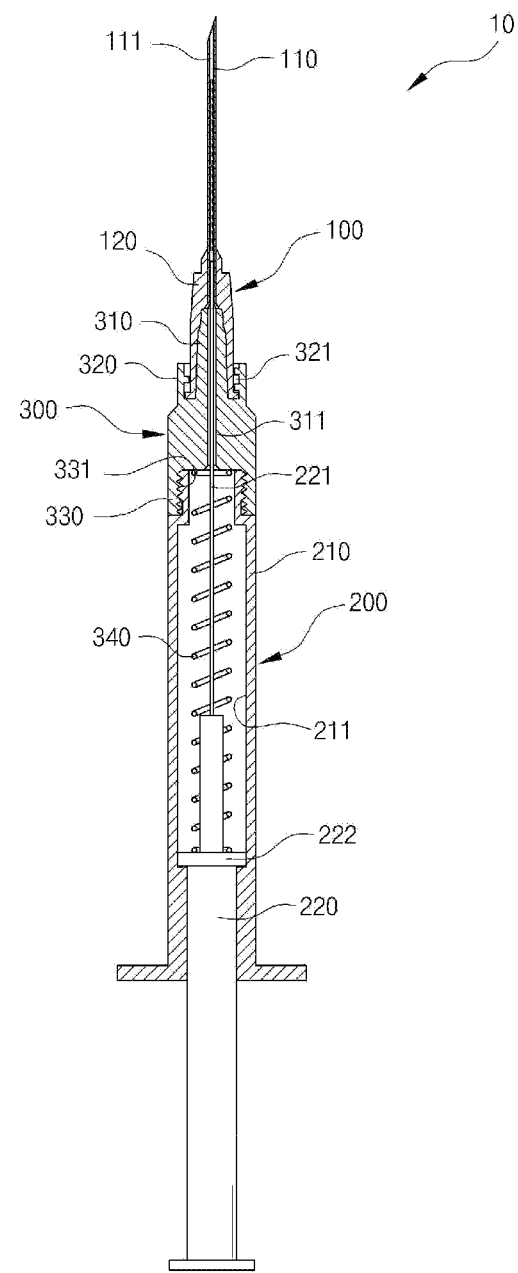
FIG. 3 is a cross-sectional view illustrating a state of the syringe of FIG. 1 before operation.
Figure 4:
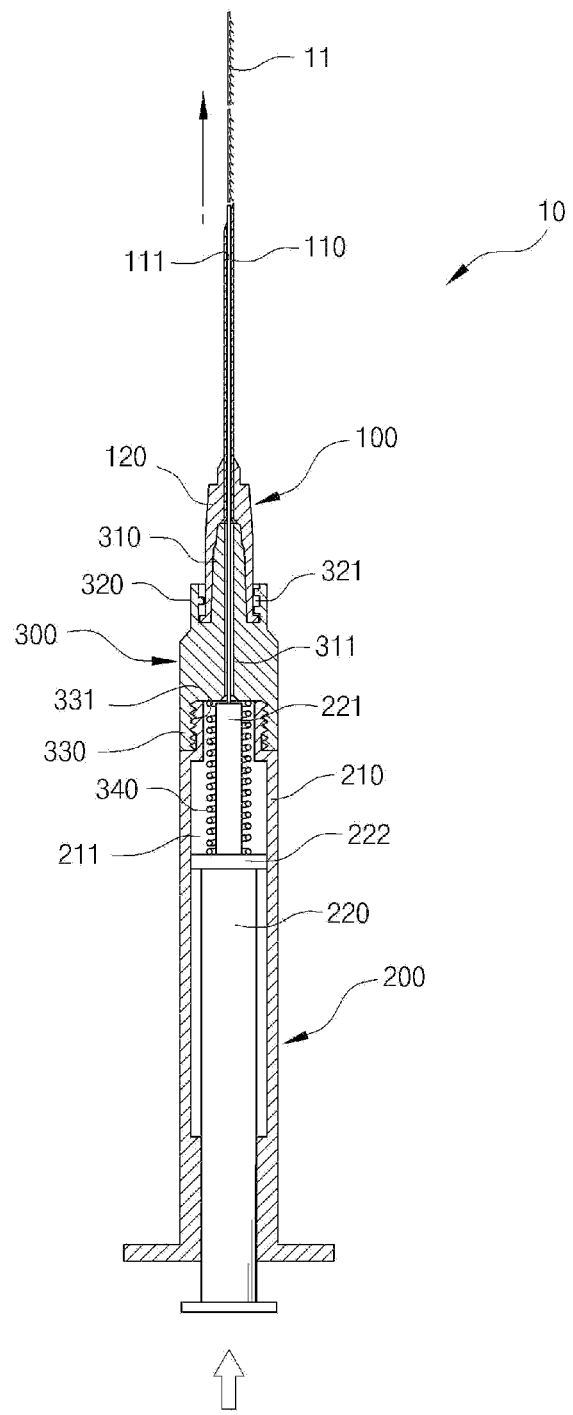
FIG. 4 is a cross-sectional view illustrating a state of the syringe of FIG. 1 after operation.
Figure 5:
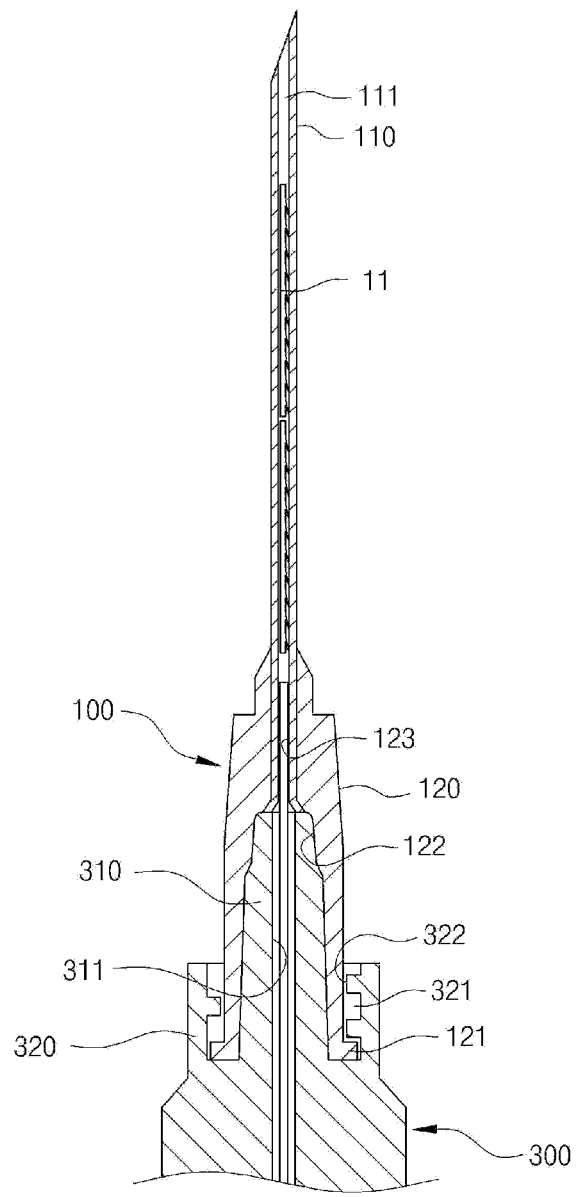
FIG. 5 is partial enlarged cross-sectional view illustrating the syringe of FIG. 1.
Figure 6:
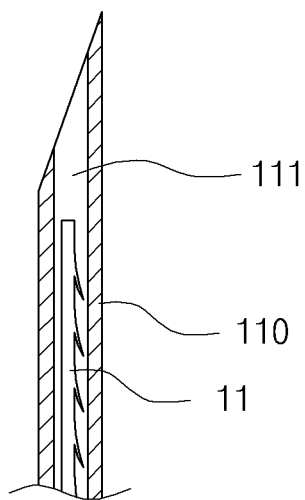
FIGS. 6a and 6b are partial enlarged cross-sectional views illustrating alternative embodiments of a needle part of the syringe of FIG. 1.
Figure 6:
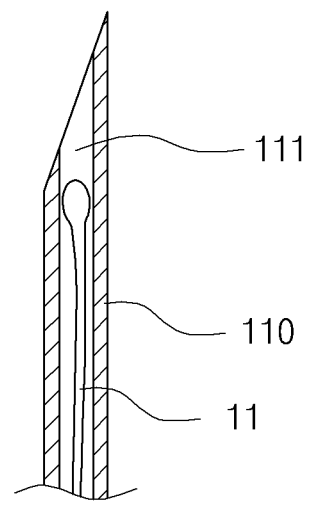
Figure 7:
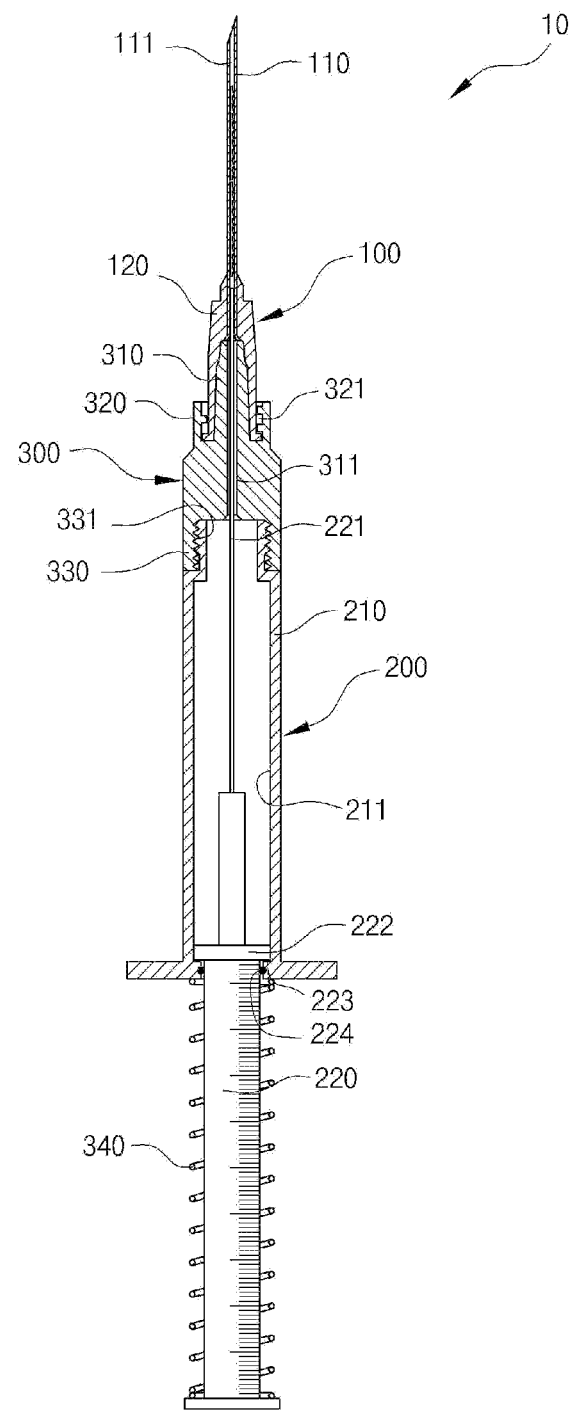
FIG. 7 is a cross-sectional view illustrating a syringe for injecting a surgical thread according to another embodiment of the present invention before operation.
Figure 8:
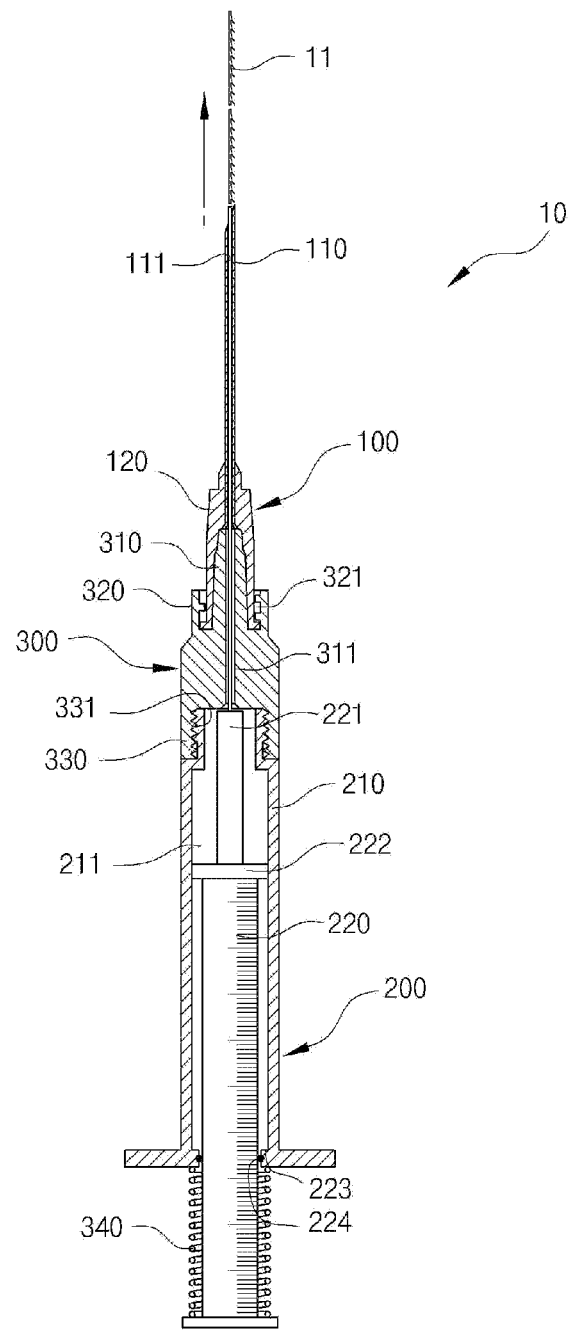
FIG. 8 is a cross-sectional view illustrating of the syringe of FIG. 7 after operation.

FIG. 1 is a perspective view illustrating a syringe for injecting a surgical thread according to an embodiment of the present invention, FIG. 2 is an exploded perspective view illustrating the syringe of FIG. 1, FIG. 3 is a cross-sectional view illustrating a state of the syringe of FIG. 1 before operation, FIG. 4 is a cross-sectional view illustrating a state of the syringe of FIG. 1 after operation, FIG. 5 is partial enlarged cross-sectional view illustrating the syringe of FIG. 1, FIGS. 6a and 6b are partial enlarged cross-sectional views illustrating alternative embodiments of a needle part of the syringe of FIG. 1, FIG. 7 is a cross-sectional view illustrating a syringe for injecting a surgical thread according to another embodiment of the present invention before operation, and FIG. 8 is a cross-sectional view illustrating of the syringe of FIG. 7 after operation.

As illustrated in FIGS. 1 through 8, the syringe 10 has a predetermined length suitable for plastic surgical treatment and is designed to inject a thin, freely bendable surgical thread 11 into a human skin tissue.

Non-limiting examples of surgical threads suitable for use in the syringe of the present invention include threads for wrinkle removal and natural and artificial hairs for hair transplantation. It should be understood that the surgical thread is intended to include all threads injected into or transplanted to skin tissues. Materials for the surgical thread include biodegradable, bioresorbable and non-bioresorbable polymers for medical applications.

The syringe 10 essentially includes a needle part 100, an injection part 200 and a connection part 300.

The needle part 100 includes a needle 110 adapted to penetrate the skin and having an injection hole 111 to accommodate a surgical thread therein.

Coupling means 120 having a coupling space 122 formed therein is coupled to one side of the needle 110. The coupling means 120 and the needle 110 are formed in one piece. A stepped latching portion 121 is formed at the front end of the outer circumference of the coupling means 120.

The coupling means 120 has a through-hole 123, which communicates with the injection hole 111 when the needle 110 is coupled to the coupling means 120. The coupling means 120 has a coupling space 122 in communication with the injection hole 111. The inner circumference of the coupling space 122 is tapered wide toward the front end of the coupling means 120 where the stepped latching portion 121 is formed.

The tapered inner circumference of the coupling space 122 facilitates coupling between the needle part 100 and the connection part 300, as will be described below.

The connection part 300 is coupled to the front end of the injection part 200 to enable coupling and decoupling of the needle part 100.

A detailed explanation of the construction of the connection part 300 will be provided below.

The connection part 300 includes: an introduction portion 310 having an inclined outer circumference adapted to be introduced into the coupling space 122 of the coupling means 120 and to allow for primary taper coupling to the needle part 100 and a connection hole 311 formed at the center thereof to be in communication with the injection hole 111 of the needle 110; a flange 320 spaced apart from the introduction portion 310 to create a fixing space 321 therebetween and having a female-threaded portion 322 formed on the inner circumference of the fixing space 321 so as to be fixedly fastened to the needle part 100 by turning operation of the stepped latching portion 121; and a fastening portion 330 integrally formed with the flange 320, having a fastening space 331 spatially isolated from the fixing space 321 and fixedly fastened to the front end of the injection part 200 in the fastening space 331.

Due to this construction, after temporal taper coupling of the introduction portion 310 in the coupling space 122 of the coupling means 120 is completed quickly, the stepped latching portion 121 of the needle part 100 is fastened to the female-threaded portion 322 formed at the front end of the connection part 300 by one rotation, thereby maintaining hermetic fixing of the needle part 100 to the injection part 200.

The connection part 300 is coupled to the front end of the injection part 200. A push needle 221 is mounted inside the injection part 200 and pushes the surgical thread 11 accommodated in the needle part 100 by the push operation of the rod 220 to inject the surgical thread 11 into a skin tissue, which will be explained below.

A detailed explanation of the construction of the injection part 200 will be provided below.

The injection part 200 includes a housing 210 having a hole 211 formed therein, a rod 220 coupled to and linearly reciprocating along the hole 211, and a push needle 221 coupled to the front end of the rod 220 and entering the injection hole 111 to cause the surgical thread to penetrate the skin.

A spring 340 is accommodated along the inner circumference of the hole 211 and is latched by a stopper 222 fixed to the outer circumference of the rod 220. The spring 340 is compressed by the connection part 300 coupled to the front end of the housing 210.

After the surgical thread 11 penetrates the skin by the action of the rod 220, the elastic force of the spring 340 elastically drives the rod 220 backward from the housing 210, making the rod 220 ready for the penetration of a next surgical thread 11.

Consequently, the needle part 100 adapted to penetrate the skin while accommodating the surgical thread 11 is coupled to or decoupled from the injection part 200 by turning after the temporal taper coupling between the needle part 100 and the connection part 300, ("push down & turn"), simultaneously ensuring ease of coupling and hermetic fixing of the needle part 100. In contrast, frequent exchange of needle parts is inevitable in conventional syringes for injecting surgical threads. Therefore, the needle part 100 can be quickly replaced with an extra needle part accommodating a new surgical thread, thus shortening the time needed to inject the surgical thread.

FIGS. 7 and 8 illustrate a syringe for injecting a surgical thread according to another embodiment of the present invention.

As illustrated in FIGS. 7 and 8, the rod 220 is coupled to and exposed outside the hole 211. The spring 340 is elastically coupled between one end of the housing 210 and a stop portion 225 formed at the distal end of the rod 220.

A closing stop 223 is formed at the inlet end of the hole 211 to restrict the moving distance of the rod 220, together with the stopper 222 formed at the front end of the rod 220.

A sealing ring 224 is coupled to one end of the closing stop 223 to maintain a closed state of the hole 211.

That is, one side of the rod 220 is coupled to the hole 211 of the housing 210 and the other side thereof is exposed outside the hole 211, and the spring 340 is interposed between the housing 210 and the stop portion 225, so that the exposed state of the rod 220 from the housing can be maintained by the elastic force of the spring 340.

The spring 340 is compressed when the rod 220 is introduced into the housing 210.

Graduations are marked on the outer circumference of the rod 220. The moving distance of the rod 220 entering the hole 211 can be measured and the depth of the surgical thread 11 penetrating the skin can be estimated by reading the graduations.

Hereinafter, an explanation will be given concerning the operation of the syringe.

First, the needle part 100, in which the surgical thread 11 is accommodated, is coupled to the connection part 300 in a push down & turn motion, and the needle 110 is then injected into the skin.

Subsequently, the rod 220 is pressurized to compress the spring 340. This compression causes the push needle 221 to enter the injection hole 111 of the needle 110, and finally, the surgical thread 11 is injected into a skin tissue.

After completion of the injection of the surgical thread 11, the pressure applied to the rod 220 is removed. The rod 220 is moved backward by the resilient force of the spring.

Simultaneously with the backward movement, the needle part 100 is withdrawn from the skin, completing the injection of the surgical thread 11.

Thereafter, another needle part 100 accommodating a new surgical thread 11 is coupled to the connection part 300. The above procedure is repeated to inject the new surgical thread 11 into the skin.

According to conventional surgical treatment methods, after a surgical thread 11 penetrates the skin, another surgical thread 11 is loaded in the same syringe 10. Alternatively, extra syringes 10 loaded with surgical threads 11 may be used alternately.

As illustrated in FIGS. 6a and 6b, however, it is difficult to insert the surgical thread 11 having different configurations into the injection hole 111 of the needle 110 because of the small diameter and flexibility of the surgical thread 11, or their surface geometry.

As a consequence, much time is consumed to load new surgical threads 11, thereby extending the time for surgical treatment.

The use of a plurality of extra syringes 10 for surgical treatment is economically disadvantageous due to their high price.

According to the present invention, the needle part 100, which is a cheap disposable medical instrument, can be easily coupled to and decoupled from the syringe 10. Therefore, an operator can previously load surgical threads 11 in a plurality of needle parts 100 and can repeatedly replace only the needle parts 100, enabling rapid surgical treatment.

Although the present invention has been described herein with reference to the foregoing embodiments and accompanying drawings, the scope of the present invention is not limited to the embodiments and drawings. Therefore, it will be evident to those skilled in the art that various substitutions, modifications and changes are possible, without departing from the spirit of the invention as disclosed in the accompanying claims.

The invention claimed is:

1. A syringe for injecting a surgical thread, comprising:
   a needle part adapted to penetrate the skin while accommodating a surgical thread and comprising a needle having an injection hole to accommodate the surgical thread therein and a coupling means having a tapered coupling space formed therein to allow the needle to be coupled to one side thereof and a stepped latching portion protruding from the wide tapered end of the coupling space;
   a connection part connected to the needle part by taper coupling and fixedly fastened to the needle part by turning operation of the needle part; and
   an injection part coupled to the connection part at the front end of a housing having a hole formed therein to allow a push needle coupled to the front end of a rod coupled to and linearly reciprocating along the hole and cooperating with the rod to push the surgical thread accommodated in the needle part and to inject the surgical thread into a skin tissue in a syringe operation manner,
   wherein the connection part comprises:
   an introduction portion having an inclined outer circumference adapted to be introduced into the coupling space of the coupling means to allow for primary taper coupling to the needle part and a connection hole formed at the center thereof to be in communication with the injection hole of the needle;
   a flange spaced outwardly from the introduction portion to create a fixing space therebetween and having a female-threaded portion formed on the inner circumference of the fixing space so as to be fixedly fastened to the needle part by turning operation after the stepped latching portion is engaged with the female-threaded portion; and
   a fastening portion having a fastening space formed at the rear of the flange and fixedly fastened to the front end of the injection part in the fastening space,
   whereby, with temporal taper coupling of the introduction portion in the coupling space of the coupling means, coupling of the connection part and the coupling means is completed in a quick and precise manner, and the injection hole and the connection hole precisely communicate with each other so that the push needle can precisely enter the injection hole; and the stepped latching portion of the needle part is fastened to the female-threaded portion formed at the front end of the connection part, thereby maintaining hermetic fixing of the needle part to the injection part.

2. The syringe according to claim 1, wherein the injection part comprises a housing having a hole formed therein, and
   a rod coupled to and linearly reciprocating along the hole.

3. The syringe according to claim 2, wherein a spring is accommodated along the inner circumference of the hole of the housing, is latched by a stopper fixed to the outer circumference of the rod, and is compressed by the coupling between the injection part and the connection part so that the push and push-back operation of the rod in the injection part is elastically maintained.

4. The syringe according to claim 2, wherein the rod is coupled to and exposed outside the hole of the housing and a spring is elastically coupled between one end of the housing and a stop portion formed at the distal end of the rod, and a closing stop is formed at the inlet end of the hole of the housing to restrict the moving distance of the rod, together with a stopper formed at the front end of the rod.

5. The syringe according to claim 4, wherein the rod has graduations marked at regular intervals on the outer circumference thereof.

* * * * *